United States Patent
Sakai et al.

(10) Patent No.: US 8,340,395 B2
(45) Date of Patent: Dec. 25, 2012

(54) DEFECT INSPECTION METHOD AND APPARATUS THEREFOR

(75) Inventors: Kaoru Sakai, Yokohama (JP); Shunji Maeda, Yokohama (JP)

(73) Assignee: Hitachi High-Technologies Corporation, Tokyo (JP)

( * ) Notice: Subject to any disclaimer, the term of this patent is extended or adjusted under 35 U.S.C. 154(b) by 286 days.

(21) Appl. No.: 12/470,507

(22) Filed: May 22, 2009

(65) Prior Publication Data

US 2009/0290783 A1 Nov. 26, 2009

(30) Foreign Application Priority Data

May 23, 2008 (JP) ................................. 2008-134944

(51) Int. Cl.
*G06K 9/00* (2006.01)
(52) U.S. Cl. ........................................................ 382/149
(58) Field of Classification Search .................. 382/141, 382/144, 145, 149; 250/559.01, 559.04, 250/559.05, 559.07, 559.08; 348/125, 129, 348/130; 356/237.1, 237.2, 237.5
See application file for complete search history.

(56) References Cited

U.S. PATENT DOCUMENTS

| | | | | |
|---|---|---|---|---|
| 6,797,975 B2 * | 9/2004 | Nishiyama et al. | ...... | 250/559.04 |
| 7,664,608 B2 * | 2/2010 | Urano et al. | .................... | 702/40 |
| 2005/0147287 A1 * | 7/2005 | Sakai et al. | .................... | 382/141 |
| 2008/0292176 A1 * | 11/2008 | Sakai et al. | .................... | 382/144 |
| 2008/0297783 A1 * | 12/2008 | Urano et al. | ............... | 356/237.5 |

FOREIGN PATENT DOCUMENTS

| | | | |
|---|---|---|---|
| JP | 05-264467 | | 10/1993 |
| JP | 2008020374 A | * | 1/2008 |
| JP | 2008039533 A | * | 2/2008 |

* cited by examiner

*Primary Examiner* — Michael A Lyons
(74) *Attorney, Agent, or Firm* — Antonelli, Terry, Stout & Kraus, LLP.

(57) ABSTRACT

The invention relates to a defect inspection apparatus in which images of mutually corresponding areas in identically formed patterns on a sample are compared to detect mismatched portions of the images as defects. The defect inspection apparatus includes an image comparator that creates a feature space with the use of feature quantities calculated from pixels of images acquired under different optical conditions and detects outlier values in the feature space as defects. Thus, the defect inspection apparatus can detect various defects with high sensitivity even if there are luminance differences between images of identical patterns which are attributable to the difference in wafer pattern thickness.

8 Claims, 14 Drawing Sheets

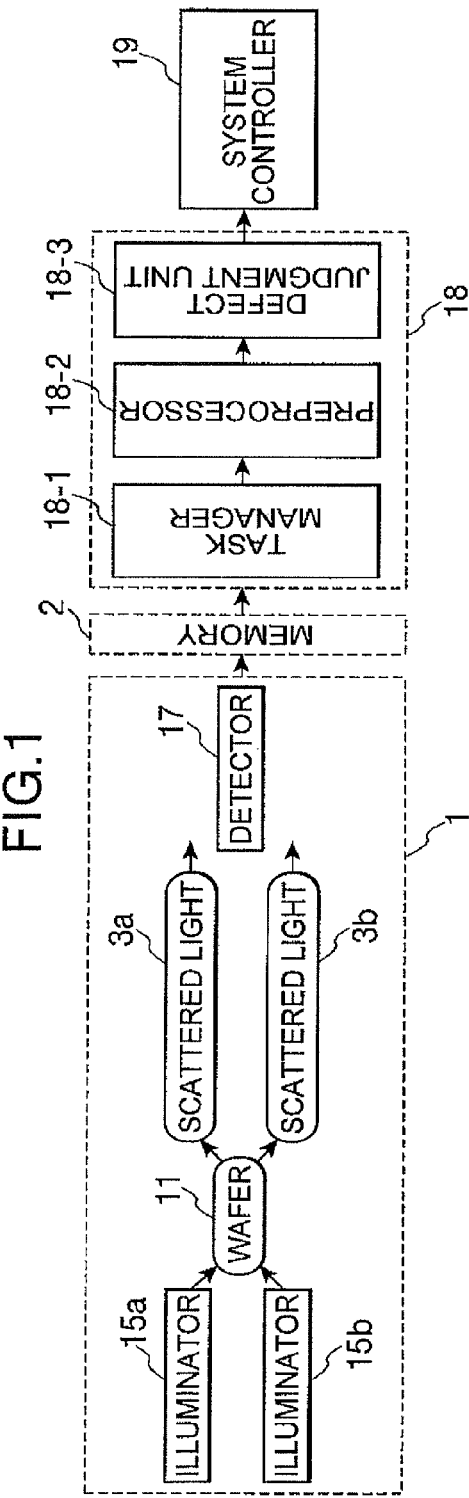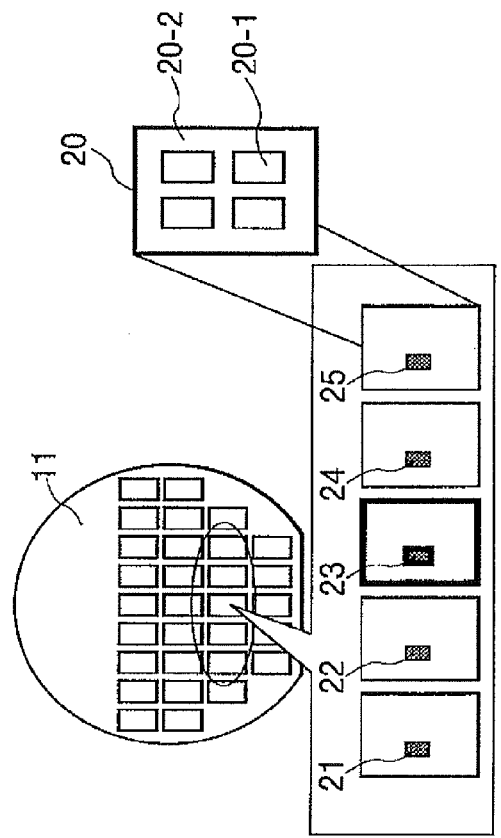

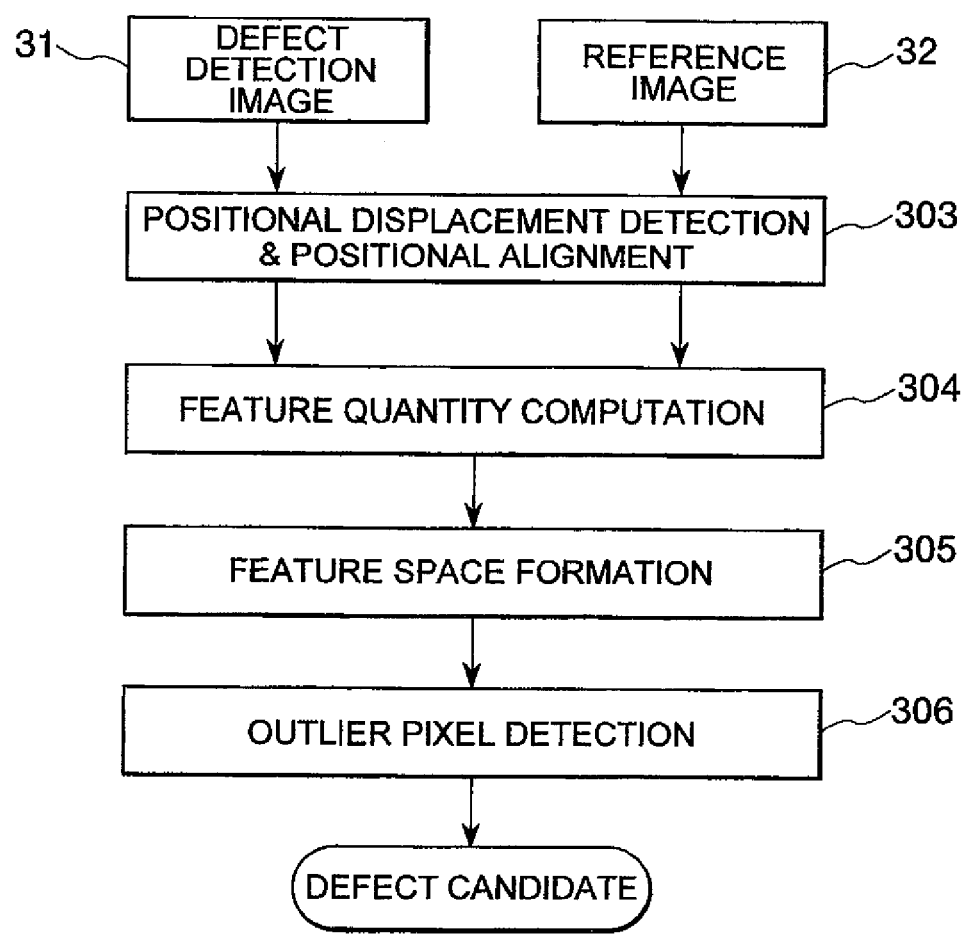

DEFECT INSPECTION METHOD AND APPARATUS THEREFOR

BACKGROUND OF THE INVENTION

The present invention relates to inspection of a sample for microscale pattern defects and foreign substances that involves comparison between images of the sample obtained with the use of illumination light, laser light, or electron beams and reference images. The invention relates particularly to an apparatus and a method for inspecting patterns suitable for external inspection of semiconductor wafers, TFTs (thin film transistors), photomasks, or the like.

One of the examples of conventional defect inspection methods involving comparison between images of an object to be inspected and reference images is disclosed in JP-A-05-264467 (Patent Document 1). In the method of Patent Document 1, a line sensor sequentially acquires images of an inspection object on which identical patterns are arranged regularly while the inspection object is moved. A particular image is then compared with an image obtained after a time interval during which the inspection object is moved by a pattern pitch, or the amount of space between two patterns. Defects are detected by detecting mismatched portions of the two images.

Such a conventional defect inspection method is further discussed below, based on the assumption that it is intended for inspection of semiconductor wafers. As shown in FIG. 2A, a sample 11 to be inspected, or a semiconductor wafer, has multiple identically-patterned chips 20 arranged thereon regularly. When the sample 11 is a memory element such as DRAM or the like, each of the chips 20 can be roughly classified into memory mats 20-1 and a peripheral circuitry area 20-2, as shown in FIG. 2B. Each of the memory mats 20-1 is a collection of tiny identical patterns (cells) whereas the peripheral circuitry area 20-2 is basically a collection of random patterns. Generally, the memory mats 20-1 are high in pattern density, and images acquired from those areas are dark. In contrast, the peripheral circuitry area 20-2 is low in pattern density, and images acquired therefrom are bright.

In a conventional pattern inspection, the inspection of the peripheral circuitry area 20-2 is such that images of mutually corresponding areas in adjacent chips (e.g., image areas 22 and 23 in FIG. 2A) are compared in terms of luminance and such that portions of those image areas with greater luminance differences than a threshold value are detected as defects. Such an inspection is hereinafter referred to as chip comparison. In contrast, the inspection of the memory mats 20-1 is such that images of adjacent cells within a memory mat 20-1 are compared in terms of luminance and such that portions of those images with greater luminance differences than a threshold value are detected as defects. Such an inspection is hereinafter referred to as cell comparison. The above two kinds of comparative inspections need be performed at high speed.

SUMMARY OF THE INVENTION

When semiconductor wafers are inspected, images of two chips, even if adjacent, may exhibit local luminance differences due to subtle differences in pattern thickness. If portions of the images with greater luminance differences than a threshold value are regarded as defects as in the above-mentioned conventional method, it thus follows that defects are extended to include areas having greater luminance differences than the threshold value simply due to the difference in pattern thickness. Because such areas, if detected as defects, misinform the user, they are not to be detected as defects. To avoid such false detection of defects, the threshold value used for defect detection has been raised conventionally. However, this means at the same time that the inspection sensitivity of the defect inspection apparatus decreases, and defects with smaller luminance differences than the raised threshold value cannot be detected. Also, the overall inspection sensitivity may decrease drastically when the threshold value is set based on local areas in which there are luminance differences due to pattern thickness, such as particular chips of a wafer or particular patterns within chips.

The inspection sensitivity is also affected by the luminance differences between chips due to variation in pattern width. In the above conventional inspection based on luminance comparison, such luminance differences may result in noise during inspection.

There are various kinds of defects; accordingly, there are defects that need not be detected (can be regarded as noise) and defects that need be detected. Although it is demanded of external inspection that only defects of the user's interest be extracted from among a great number of defects, this can hardly be achieved with the above-described comparison between the threshold value and luminance differences. In contrast, when factors dependent on samples to be inspected such as materials, surface roughness, size, and depth are combined with factors dependent on optical detector systems such as illumination conditions or the like, defects may look differently in an image.

The invention is thus a defect inspection method and a defect inspection apparatus designed to overcome the above problems associated with conventional defect inspection technologies, in which images of mutually corresponding areas in identically formed patterns on a sample are compared to detect mismatched portions of the images as defects. In accordance with the invention, the influences of luminance variation between compared images arising from the difference in layer thickness or pattern width can be reduced, and only defects of the user's interest can be detected with high sensitivity and at high speed that would otherwise be regarded as noise.

The defect inspection apparatus of the invention thus includes means for detecting, from scattered light distributions obtained under multiple optical conditions, the scattered light components that are included in the ranges of all the multiple optical conditions as an optical image and means for detecting defects with the use of images obtained under the multiple optical conditions.

Representative aspects of the invention can be summarized as below.

1) In one aspect, the invention is a defect inspection method for acquiring and comparing images of mutually corresponding areas in a plurality of identically formed patterns on a sample to detect defects, the method comprising the steps of:

illuminating the plurality of patterns on the sample under predetermined optical conditions;

detecting scattered light from the sample under predetermined optical conditions;

acquiring a plurality of images of different optical conditions; and integrating information of the plurality of images to detect defects.

2) The defect inspection method according to the aspect 1) is further defined such that:

the acquired plurality of images are divided into small images of a particular size;

the divided small images are distributed to a plurality of CPUs;

defect judgment operations are performed synchronously or asynchronously by the plurality of CPUs; and the results of the defect judgment operations are integrated to detect defects.

3) In another aspect, the invention is a defect inspection method for acquiring images of mutually corresponding areas in a plurality of identically formed patterns on a sample under a plurality of optical conditions and for detecting defects with the use of a plurality of images acquired under the plurality of optical conditions, the method comprising the steps of:

storing the plurality of images acquired under the plurality of optical conditions on a memory;

reading out the plurality of images stored on the memory with the use of a CPU for performing task management;

dividing the plurality of images read out from the memory into small images and inputting the divided small images to a plurality of arithmetic CPUs that execute tasks; and performing a plurality of defect judgment operations on the divided small images input to the plurality of arithmetic CPUs with the use of the plurality of arithmetic CPUs.

4) In still another aspect, the invention is a defect inspection apparatus for inspecting patterns formed on a sample for defects, the apparatus comprising:

an illuminator for illuminating the patterns under a plurality of illumination conditions;

means for guiding a plurality of images of the patterns to a detector under a plurality of light-receiving conditions;

a memory for storing the plurality of images acquired;

task management means for reading out the plurality of images stored from the memory, for dividing the plurality of images read out into small images, and for inputting the divided small images to a plurality of arithmetic CPUs; and means for detecting defects with the use of the divided small images input and corresponding reference images.

These and other objects, features, and advantages of the invention will be apparent from the following more particular description of preferred embodiments of the invention, as illustrated in the accompanying drawings.

BRIEF DESCRIPTION OF THE DRAWINGS

FIG. 1 is a schematic diagram illustrating a configuration of the invention.

FIG. 2A is a schematic diagram of chips on a wafer.

FIG. 2B is a schematic diagram of a chip.

FIG. 4 is a flowchart illustrating the process flow of a defect judgment unit.

DESCRIPTION OF THE PREFERRED EMBODIMENTS

Figure 3:
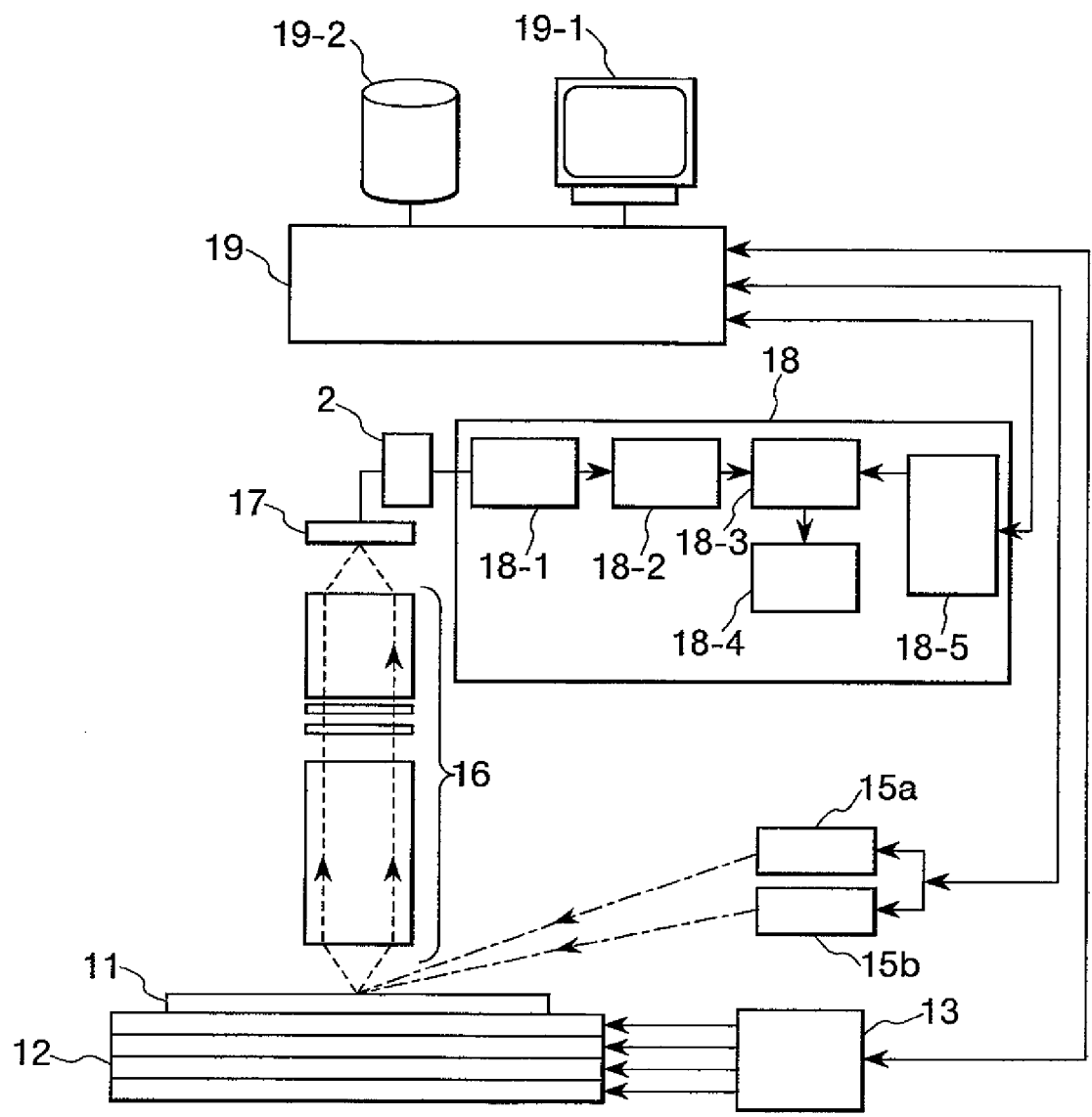
FIG. 3 schematically illustrates a defect inspection apparatus of the invention.

Preferred embodiments of the present invention are now described with reference to FIGS. 1 to 15. As an example, the defect inspection apparatuses of the embodiments are intended to employ dark-field illumination to inspect semiconductor wafers.

FIG. 1 is a schematic diagram of a defect inspection apparatus that embodies the invention. As shown in FIG. 1, an optical unit 1 structurally includes multiple illuminators 15a and 15b and a detector 17. The illuminators 15a and 15b emit illumination lights in mutually different optical conditions onto a sample 11 (i.e., a wafer to be inspected). The illumination lights emitted by the illuminators 15a and 15b onto the sample 11 result in scattered lights 3a and 3b, respectively, from the sample 11, which lights are detected as scattered-light intensity signals by the detector 17. Although FIG. 1 illustrates the single detector 17 to detect the scattered lights 3a and 3b, two detectors may instead be provided for one detector to detect the scattered light 3a and for the other to detect the scattered light 3b. Also, the number of illuminators and the number of detectors may not necessarily be two each, but can be more than two. The scattered-light intensity signals detected by the detector 17 are temporarily stored on a memory 2 and thereafter input to an image processor 18. The image processor 18 includes a task manager 18-1, an image preprocessor 18-2, and a defect judgment unit 18-3. The task manager 18-1 generates tasks, described later, for the scattered-light intensity signals stored on the memory 2, based on the size and number of chips on the sample 11 and detection conditions. The preprocessor 18-2 performs signal correction, image division based on the tasks, and the like, which will be described later. The defect judgment unit 18-3 performs defect judgment operation, described later, based on the tasks generated by the task manager 18-1 and outputs defect information to a system controller 19.

The scattered lights 3a and 3b, as used herein, refer specifically to the distributions of the scattered lights generated by the illuminators 15a and 15b. The scattered lights 3a and 3b will differ from each other, depending on the optical conditions of the illumination lights emitted from the illuminators 15a and 15b. In this specification, the optical properties or characteristics of scattered light generated by an illuminator is referred to as the distributions of the scattered light. More specifically, the scattered-light distributions are the distributions of optical parameters such as intensity, amplitude, phase, polarization, wavelength, coherence, or the like, with respect to the emission position, emission direction, and emission angle of the scattered light.

FIG. 3 schematically illustrates more in detail the defect inspection apparatus that has the configuration shown in FIG. 1.

This defect inspection apparatus according to the invention includes the multiple illuminators 15a and 15b that emit illumination light obliquely onto the sample 11 such as a semiconductor wafer; an optical detector system 16 that focuses vertically-scattered light from the sample 11; the detector 17 that receives the focused light and converts it to an image signal; the memory 2 that stores the image signal; the image processor 18; and the system controller 19. The sample 11 is placed on a stage 12 which is driven by a mechanical controller 13 such that the stage 12 moves and rotates in X and Y planes and moves in a Z direction. By moving the three-dimensionally-driven stage 12 horizontally with the sample 11 placed thereon and detecting scattered light from foreign substances or defects on the sample 11, the detection results are obtained as two-dimensional images.

Light sources for the illuminators 15a and 15b can be lasers or lamps. The wavelength of the light of the illumination sources can be short or in a wide range (white light). When short-wavelength light is to be used, it can be ultraviolet light (UV light) for the purpose of increasing the resolution of defect detection images (i.e., for the purpose of detecting microscale defects). When single-wavelength lasers are to be used as the light sources, the illuminators 15a and 15b can have means for reducing the coherence of the laser light (not illustrated in FIG. 3).

The detector 17 is a time delay integration image sensor (TDI image sensor) in which multiple one-dimensional image sensors are arrayed two-dimensionally. Each of the one-dimensional image sensors detects a signal in synchronous with the movement of the stage 12 and transfers the detected signal to a one-dimensional image sensor located at its subsequent stage for the purpose of signal integration. This allows for acquisition of two-dimensional images at relatively high speed and with relatively high sensitivity. The use of a parallel-output TDI image sensor with multiple output taps enables even faster detection because outputs from the sensor can be processed in parallel.

The image processor 18 extracts defect candidates located on the sample 11. The image processor 18 includes the task manager 18-1, the preprocessor 18-2, the defect judgment unit 18-3, a defect classifier 18-4, and a parameter setter 18-5. The task manager 18-1 generates and manages inspection tasks based on the design information, type, and process flow of the sample 11 (semiconductor wafer). The preprocessor 18-2 performs image correction, such as shading correction and dark-level correction, on input image signals and divides the images based on the tasks. The defect judgment unit 18-3 extracts defect candidates from the corrected and divided images. The defect classifier 18-4 classifies the extracted defect candidates into several kinds. The parameter setter 18-5 receives externally input parameters for image processing and transfers them to the defect judgment unit 18-3.

At the defect judgment unit 18-3, the defect candidate extraction is performed in the following manner. First, a correction amount is calculated to perform positional alignment between a corrected and input image of a location of interest on the sample 11 (hereinafter referred to as "defect detection image") and another image of the same location (hereinafter referred to as "reference image"). Secondly, the defect detection image and the reference image are aligned with the use of the calculated correction amount. Thirdly, a feature space is created with the use of the feature quantities of relevant pixels. Lastly, outlier pixels in the feature space are detected and output as defect candidates.

The system controller 19 includes therein a CPU for various controls and is connected to a user interface 19-1 and a storage device 19-2. The user interface 19-1 has input means for receiving, from the user, inspection parameters (the kinds of feature quantity used for distinguishing between defects and noise, threshold values, and the like, which are described later in detail) and the design information of the sample 11. The user interface 19-1 also has output means for displaying defect information. The storage device 19-2 stores the feature quantities and images of defect candidates. The mechanical controller 13 moves the stage 12 in response to a control instruction from the system controller 19. The image processor 18 and the optical detector system 16 are also driven based on an instruction from the system controller 19.

As already shown in FIGS. 2A and 2B, the sample 11, or a semiconductor wafer, has the multiple identically-patterned chips 20 aligned thereon, each of which includes the memory mats 20-1 and the peripheral circuitry area 20-2. The system controller 19 continuously moves this sample 11 with the use of the stage 12 and sequentially captures images of the chips 20 with the use of the detector 17 while moving the stage 12. Thereafter, the system controller 19 compares a defect detection image against reference images. In this case, when that defect detection image is assumed to be, for example, a digital image signal of an area 23 of one of the defect detection images in FIG. 2A, the reference images are digital image signals of areas 21, 22, 24, and 25 of the defect detection images. By comparing a pixel of the defect detection image against the corresponding pixels of the reference images and other pixels within the defect detection image that includes the area 23, pixels significantly different in characteristics are detected as defect candidates.

With reference now to FIG. 4, the process flow of the defect judgment unit 18-3 is described, in which the area (image) 23 in FIG. 2A is used as a defect detection image. First, the defect detection image, designated 31 in FIG. 3, and a corresponding reference image 32 (in this case, the area 22 of FIG. 2A) are read out from the memory 2. The positional displacement between the two is detected to perform positional alignment (Step 303). The positional displacement detection can be performed by moving one of the images relative to the other to obtain the displacement in which the sum of squares of the luminance differences between the two is the smallest or by obtaining the displacement in which their normalized correlation coefficient is the largest. After the positional alignment, multiple feature quantities are calculated using the pixels of the defect detection image 31 and their corresponding pixels of the reference image 32 (Step 304). The feature quantities can be any quantity as long as it represents the characteristics of the pixels. Examples of the feature quantities include luminance; contrast; grayscale difference; the luminance variance of adjacent pixels; correlation coefficients; increase and decrease in luminance relative to adjacent pixels; and quadratic differential values. Some of the above examples are given by the following formulas when the luminance of each pixel of the defect detection image is represented by $f(x, y)$ and the luminance of each corresponding pixel of the reference image is represented by $g(x, y)$.

Luminance: $f(x,y)$ or $\{f(x,y)+g(x,y)\}/2$ [Formula 1]

Contrast: $\max\{f(x,y),f(x+1,y),f(x,y+1),f(x+1,y+1)\} - \min\{f(x,y),f(x+1,y),f(x,y+1),f(x+1,y+1)\}$ [Formula 2]

Grayscale difference: $f(x,y)-g(x,y)$ [Formula 3]

Variance: $[\Sigma\{f(x+i,y+j)^2\}-\{\Sigma f(X+i,y+j)\}^2/M]/(M-1)$, where $i$ and $j=-1, 0,$ or $1$, and $M=9$. [Formula 4]

By marking some or all of the above feature quantities of each pixel in a space whose axes represent the selected feature quantities, a feature space is formed (Step 305). Finally, defect candidates are obtained by detecting pixels located outside a data distribution in the feature space, that is, outlier pixels (Step 306).

Figure 5A:
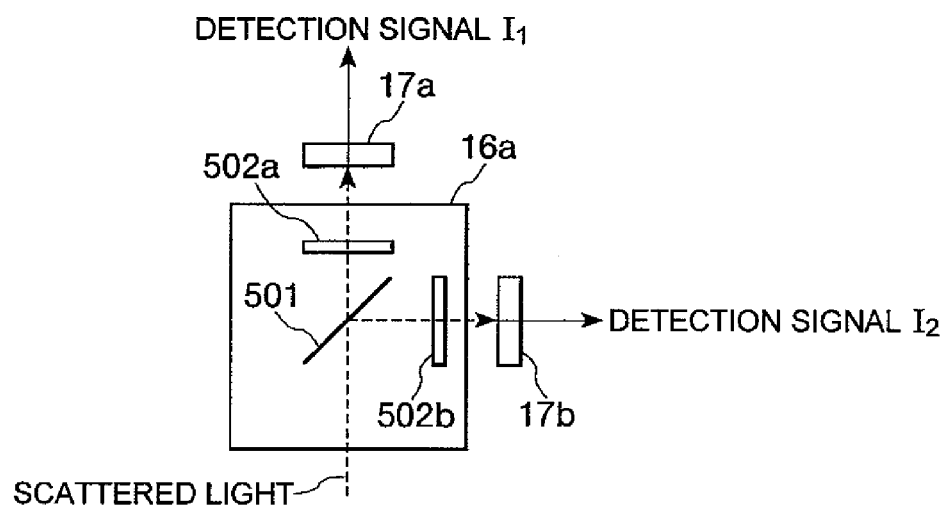
FIG. 5A is a schematic diagram of a detector capable of detecting multiple optical components collectively.
Figure 5B:
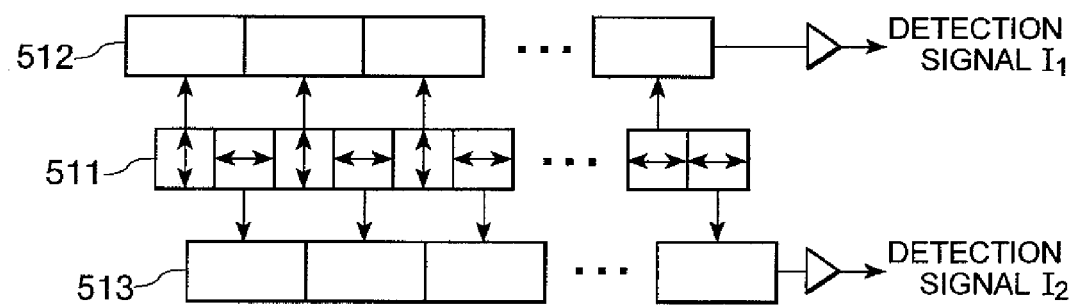
FIG. 5B is a schematic diagram of a detector that acquires multiple detection signals of mutually different polarization components.

The present invention is also capable of integrating images of different optical conditions in performing defect judgment operation. FIGS. 5A and 5B show examples of other detectors which are effective in such cases and capable of detecting multiple optical components collectively.

FIG. 5A illustrates an example in which a polarizing beam splitter 501 splits scattered light into two beams of different polarization states and detectors 17a and 17b detect the beams. Wave plates 502a and 502b are provided in an optical detector system 16a, if necessary, to select desired polarization states. When an optical element having wavelength selection functions such as a dichroic mirror or the like is provided in place of the polarizing beam splitter 501, this is equivalent to a three-plate CCD sensor. In this case, scattered light having multiple wavelengths can be separated according to the wavelengths, and the separated light beams can be detected individually.

FIG. 5B illustrates an example of a detector that acquires multiple detection signals of mutually different polarization components by detecting different polarization states with light-receiving pixels of the detector. Each of linearly-arrayed light-receiving pixels 511 has a polarizer arranged thereon, but the direction in which a polarizer is arranged on a particular pixel is different from the direction in which a polarizer is arranged on its adjacent pixel so that different polarization states can be detected at the two pixels. Such a detector is constructed by attaching an array of polarizers to the pixels of a linear sensor, as disclosed in Japanese Patent No. 3325825. As shown by the detector of FIG. 5B, which is intended as a linear CCD sensor, when the signals from odd-numbered pixels and the signals from even-numbered pixels are output to a horizontal transfer register 512 and a horizontal transfer register 513, respectively, the registers 512 and 513 can output detection signals of different polarization components. The detector of FIG. 5A is capable of achieving higher image resolution than the detector of FIG. 5B, yet the detector of FIG. 5B is less costly than the detector of FIG. 5A since only one sensor is required.

The foregoing examples illustrate two methods for collectively acquiring multiple optical components, one involving the use of multiple detectors, the other involving the use of a single detector. Alternatively, images can be acquired sequentially with illumination and light-receiving conditions changed and can be temporarily stored on the memory 2 shown in FIG. 1, so that the image processor 18 performs defect judgment operation after images of all the optical conditions are acquired.

Because images are acquired continuously while the stage 12 shown in FIG. 3 is moving, the images need to be divided into small images of a particular size to perform defect judgment operation.

Figure 6A:
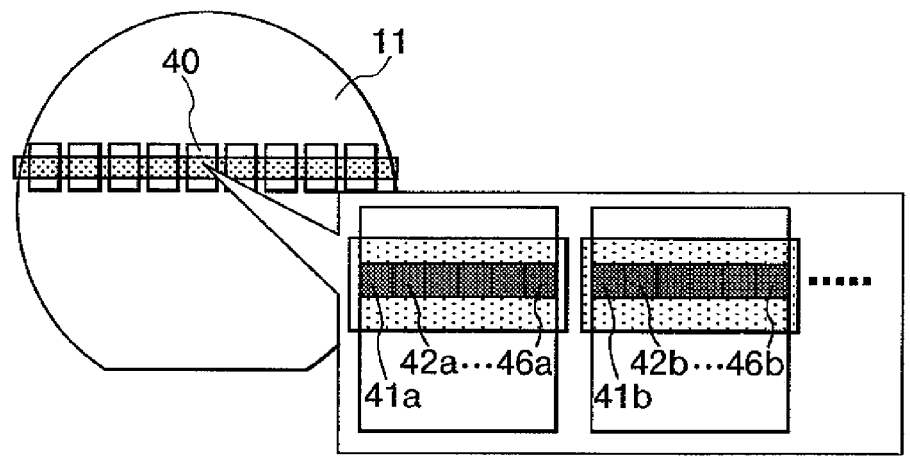
FIG. 6A is a schematic diagram illustrating an example of image acquisition with the use of a detector.

FIG. 6A illustrates an example in which a chip 40 on the sample (semiconductor wafer) 11 is inspected and images of the chip 40 are acquired by a detector. In this example, the images of the chip 40 are acquired under multiple optical conditions and stored on the memory 2 shown in FIG. 1. The task manager 18-1 reads out the images from the memory 2 and divides an image of the chip 40 acquired under optical condition A into six small images 41a to 46a and an image of the chip 40 acquired under optical condition B into six small images 41b to 46b, as shown in FIG. 6A. Each set of the small images 41a and 41b, 42a and 42b, ..., and 46a and 46b is a set of images of the same area in the chip 40. The task manager 18-1 then outputs these sets of the small images, each of which has been acquired under different optical conditions but from the same area in the chip 40, to the preprocessor 18-2 for preprocessing such as shading correction and the like. Thereafter, defect judgment operation is performed with the use of the corrected small images. In this example, an image of the chip 40 is assumed to be divided into six small images, but the division number is not limited to six. The division number can be any number as long as it is plural.

Figure 6B:
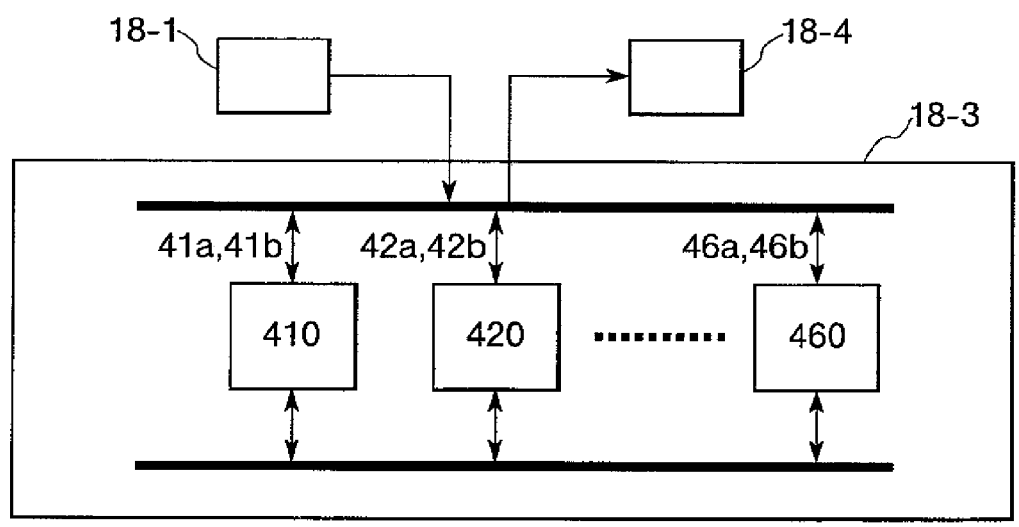
FIG. 6B schematically illustrates an exemplary system configuration of an image processor that performs image division, image preprocessing, and defect judgment operation.

FIG. 6B illustrates an exemplary system configuration of the image processor 18 in which image division, preprocessing, defect judgment operation are performed. The image processor 18 includes the task manger 18-1 (CPU) that generates and manages tasks, described later in detail, and six arithmetic CPUs 410 to 460 that perform preprocessing and defect judgment operation. The task manager 18-1 divides each image acquired under different optical conditions into six small images such that each small image in an image has its own counterpart in another image. These divided small images are distributed to the arithmetic CPUs 410 to 460. The arithmetic CPUs 410 to 460 and the task manager 18-1 (CPU) are mutually connected by a data-transfer bus. The arithmetic CPUs 410 to 460 can perform not only the same operation in parallel but different operations in parallel. Tasks for these arithmetic CPUs 410 to 460 are managed by the task manager CPU 18-1.

Figure 7A:
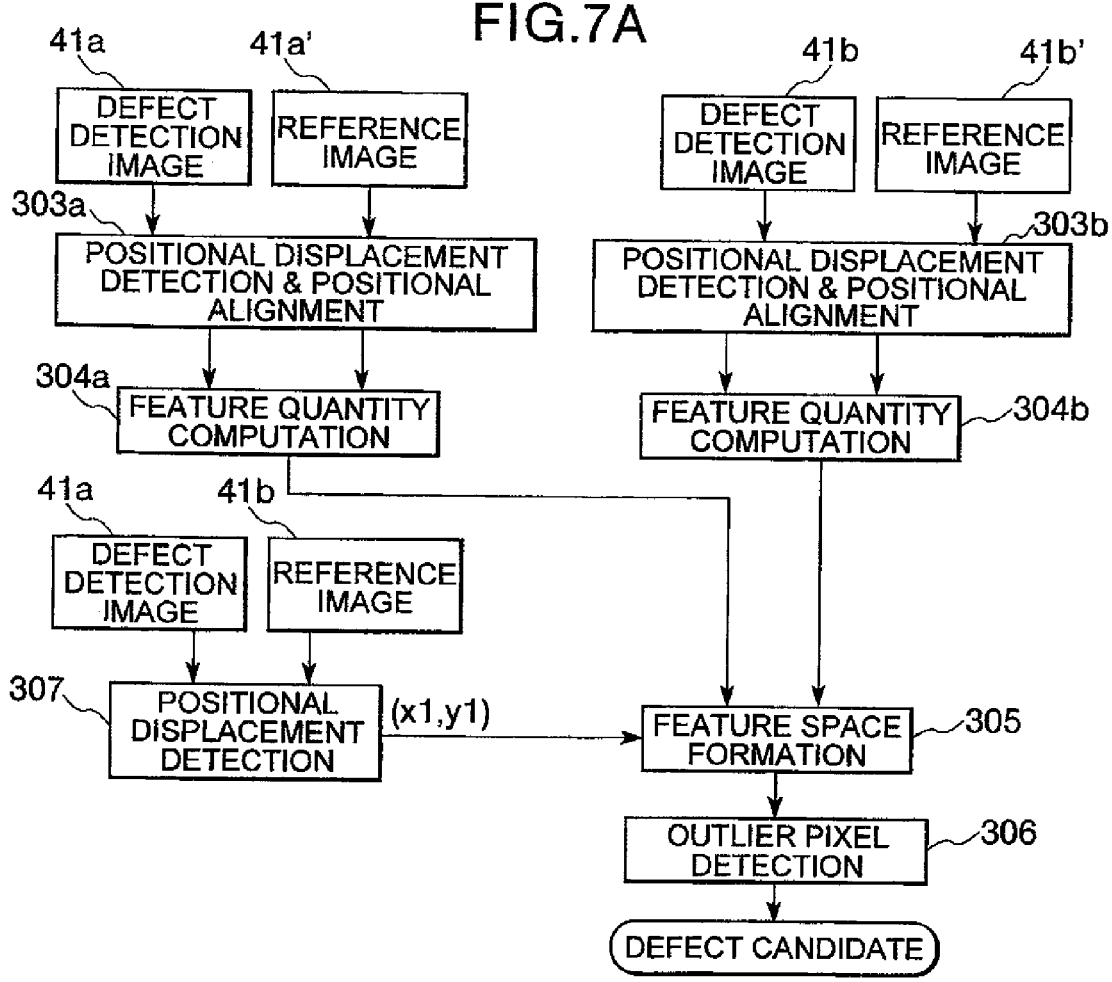
FIG. 7A is a flowchart illustrating the process flow of defect judgment operation with the use of images acquired under multiple optical conditions.

With reference now to FIG. 7A, another process flow of defect detection, different from the one shown in FIG. 4, is discussed in which defects are detected from two images acquired under different optical conditions. The foregoing arithmetic CPUs 410 to 460 each receive a set of two divided images acquired under different optical conditions and from the same area in the chip 40 to perform defect judgment operation. First, the positional displacement between the divided image (defect detection image) 41a of the chip 40 acquired under optical condition A and its reference image 41a' is calculated to perform positional alignment (Step 303a). After the positional alignment, feature quantities are calculated using the pixels of the defect detection image 41a and their corresponding pixels of the reference image 41a' (Step 304a). Likewise, the divided image (defect detection image) 41b of the chip 40 acquired under optical condition B and its reference image 41b' are subjected to positional alignment (Step 303b) and feature quantity calculation (Step 304b). If the defect detection images 41a and 41b of optical condition A and B, respectively, have been acquired at different times, the positional displacement between the defect detection images 41a and 41b is also calculated (Step 307). Thereafter, a feature space is formed by selecting all or some of the feature quantities while considering the positional relationship between the defect detection images 41a and 41b (Step 305). As stated earlier, the feature quantities, calculated from each set of a defect detection image and a reference image, are selected from among luminance, contrast, grayscale difference, the luminance variance of adjacent pixels, correlation coefficients, increase and decrease in luminance relative to adjacent pixels, and quadratic differential values. In addition, the feature quantities include the luminance itself of each image (41a, 41a', 41b, and 41b'). It is also possible to integrate the two defect detection images 41a and 41b and integrate the two reference images 41a' and 41b', that is, obtain the average value of the defect detection images 41a and 41b and the average value of the reference images 41a' and 41b' to calculate one or more of the above feature quantities.

Assume here that the average Ba of luminance between the defect detection image 41a and the reference image 41a' and the average Bb of luminance between the defect detection image 41b and the reference image 41b' are calculated as the feature quantities. When the positional displacement between the defect detection images 41a and 41b is expressed as (x1, y1) and the average (feature quantity) Ba as (x, y), the average (feature quantity) Bb can be expressed as (x+x1, y+y1). Thus, a feature space is created by marking the values of all the pixels in a two-dimensional space with X values being Ba (x, y) and Y values being Bb (x+x1, y+y1).

Figure 7B:
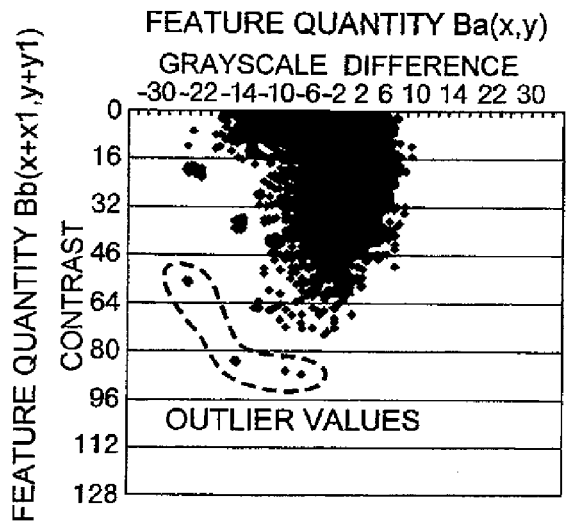
FIG. 7B is a schematic diagram of a feature space generated.

FIG. 7B is an example of the feature space created. Pixels with outlier values off from a densely-packed distribution in this two-dimensional space are detected as defect candidates. This defect detection can be performed with the use of a two-dimensional Gaussian distribution and a standard deviation. Alternatively, it can be performed in an N-dimensional feature space formed with an N number of feature quantities.

As explained above, defect judgment operation according to the present invention is performed by inputting, to each of the arithmetic CPUs, multiple image signals obtained from scattered lights generated under different optical conditions. As can be expected, two images obtained under different optical conditions differ in scattered-light distribution, and the kinds of defects detected from the two images also differ slightly. Thus, by integrating information of different optical conditions in detecting defects, various kinds of defects can be detected collectively.

Figure 8:
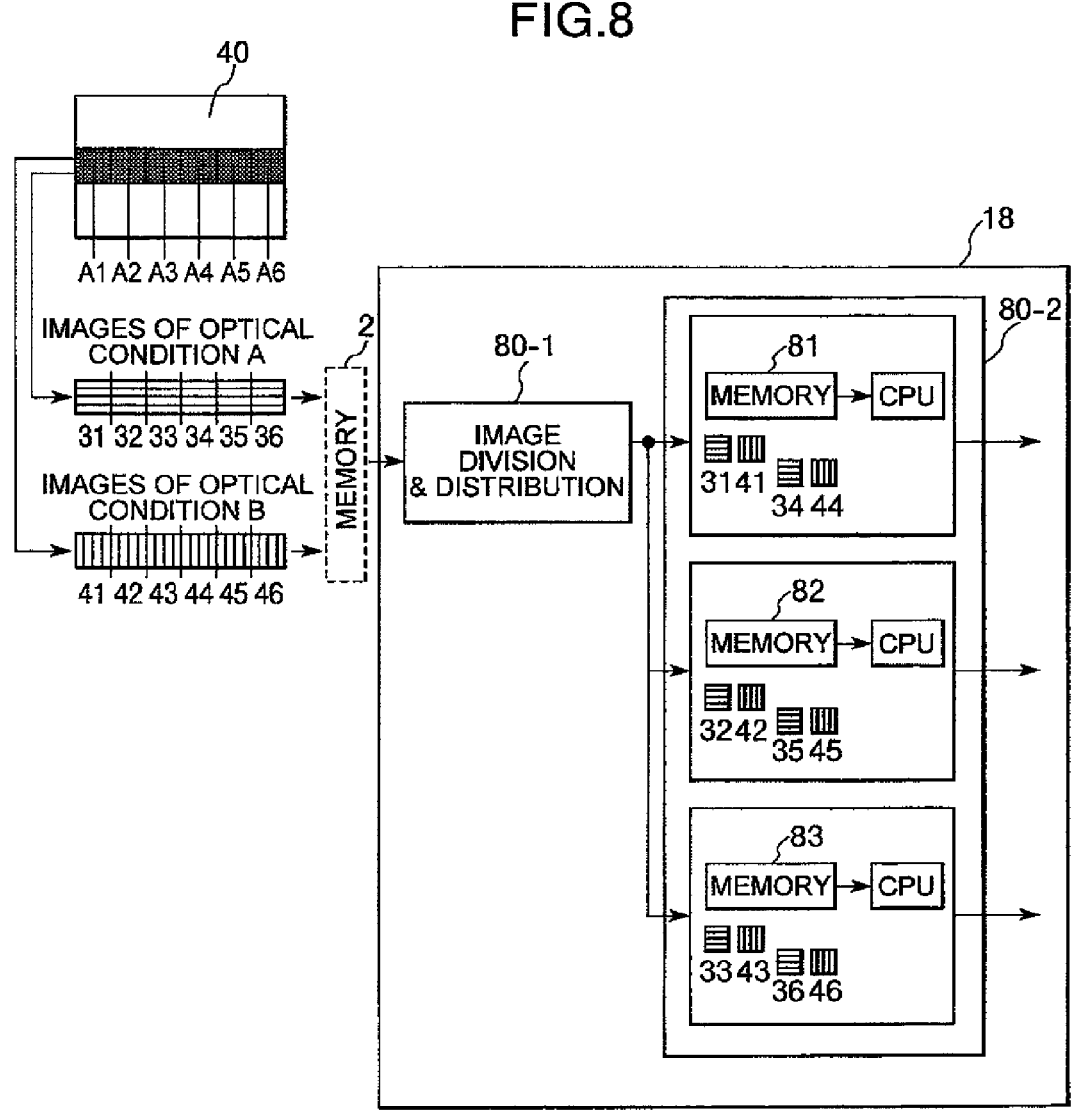
FIG. 8 is a schematic diagram illustrating the process flows of image distribution and parallel defect judgment operations with the use of multiple CPUs.

FIG. 8 illustrates another configuration of the image processor 18 according to the invention. The shaded area of the chip 40 is an area to be inspected, and multiple images are acquired under different optical conditions (optical conditions A and B) at the same time or at different times and stored on the memory 2. A task manger CPU 80-1 inside the image processor 18 reads out the images from the memory 2 and divides them to distribute them to an arithmetic unit 80-2 including three arithmetic CPUs that perform image preprocessing and defect judgment operation. As shown in FIG. 8, the arithmetic CPUs inside the arithmetic unit 80-2 each include a memory, designated 81, 82, and 83 in FIG. 8. Thus, the divided images distributed to the three arithmetic CPUs can be stored on their respective memories 81, 82, and 83. In this example, it is assumed that a defect detection image is divided into six small images and that the six small images are distributed to the three arithmetic CPUs to perform defect judgment operations in parallel. First, the three arithmetic CPUs receive divided defect detection images 31, 32, and 33 of optical condition A corresponding to three areas A1, A2, and A3, respectively, which are located from left to right in the shaded area of the chip 40, and divided defect detection images 41, 42, and 43 of optical condition B corresponding to the areas A1, A2, and A3, respectively, and their corresponding reference images (not shown in FIG. 8) to start defect judgment operations. Meanwhile, defect detection images corresponding to the remaining three areas A4, A5, and A6 are stored on the memories 81, 82, and 83, respectively. After completing the defect judgment operations for the defect detection images of the areas A1, A2 and A3, the three arithmetic CPUs read out the defect detection images corresponding to the areas A4, A5, and A6 from the memories 81, 82, and, 83, respectively, to start defect judgment operation. If the memories 81, 82, and 83 are not to be provided for the arithmetic CPUs, the defect detection images corresponding to the areas A4, A5, and A6 are input to the arithmetic CPUs after the defect judgment operations for the images of the areas A1, A2, and A3 are complete.

Figure 9:
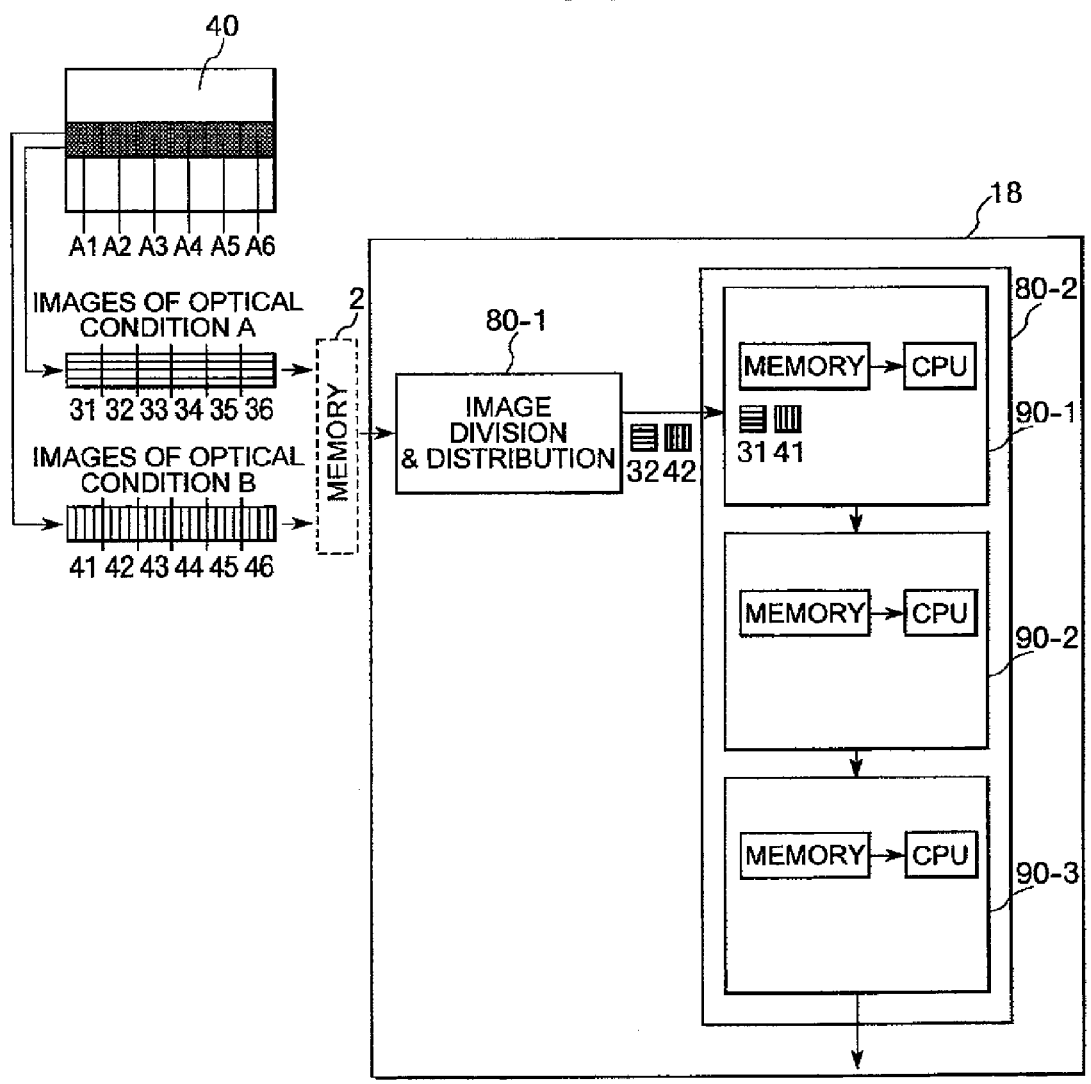
FIG. 9 a schematic diagram illustrating the process flows of image distribution and sequential defect judgment operations with the use of multiple CPUs.

As above, FIG. 8 illustrates a case in which images of different areas are input to three arithmetic CPUs, and similar defect judgment operations are performed in parallel. The image processor according to the invention, however, is not limited to the above case but also applicable to cases where a set of images acquired from the same area is sequentially subjected to defect judgment operation by the three arithmetic CPUs. FIG. 9 illustrates such cases. Firsts the images 31 and 41 corresponding to the leftmost area A1 in the chip 40 are input to a CPU 90-1. The CPU 90-1 then performs preprocessing on the input images and outputs the resultant images to a CPU 90-2. Thereafter, the CPU 90-1 receives and performs preprocessing on the images 32 and 42 corresponding to the area A2. Meanwhile, the CPU 90-2 calculates the positional displacements between the input images corresponding to the area A1 and their respective reference images to generate positionally-corrected images and output them to a CPU 90-3. Thereafter, the CPU 90-2 receives the images corresponding to the area A2 from the CPU 90-1 and performs positional displacement calculation and positional correction on them. The CPU 90-3 calculates feature quantities from the positionally-corrected input images to detect pixels representing defect candidates. Thereafter, the CPU 90-3 receives the images corresponding to the area A2 and performs the same defect judgment operation on them. In this way, the three arithmetic CPUs performs mutually different tasks, and images of the same area are sequentially passed on to the arithmetic CPUs for defect judgment operation.

The image processor 18 according to the invention is also capable of performing multiple kinds of defect judgment operations in parallel. As mentioned earlier with reference to FIG. 2B, the chip 20 to be inspected has the memory mats 20-1 and the peripheral circuitry area 20-2. Each of the memory mats 20-1, a collection of tiny identical patterns (cells), should be compared with adjacent cells, which are less subject to the influences of wafer surface irregularities, rather than with its counterpart in an adjacent chip 20 because noise can be reduced, and defects can be detected more easily. Such comparison is called cell comparison. Also in the cell comparison, similar to the foregoing defect judgment operations involving chip comparison, feature quantities are calculated among pixels within a defect detection image, in which a pixel is compared with a pixel located away from that pixel by a cell pitch. Then, outlier pixels in a feature space are detected as defect candidates. Also applicable in the case is simple binarization processing, in which pixels with greater feature quantity differences than a threshold value are detected.

Figure 10A:
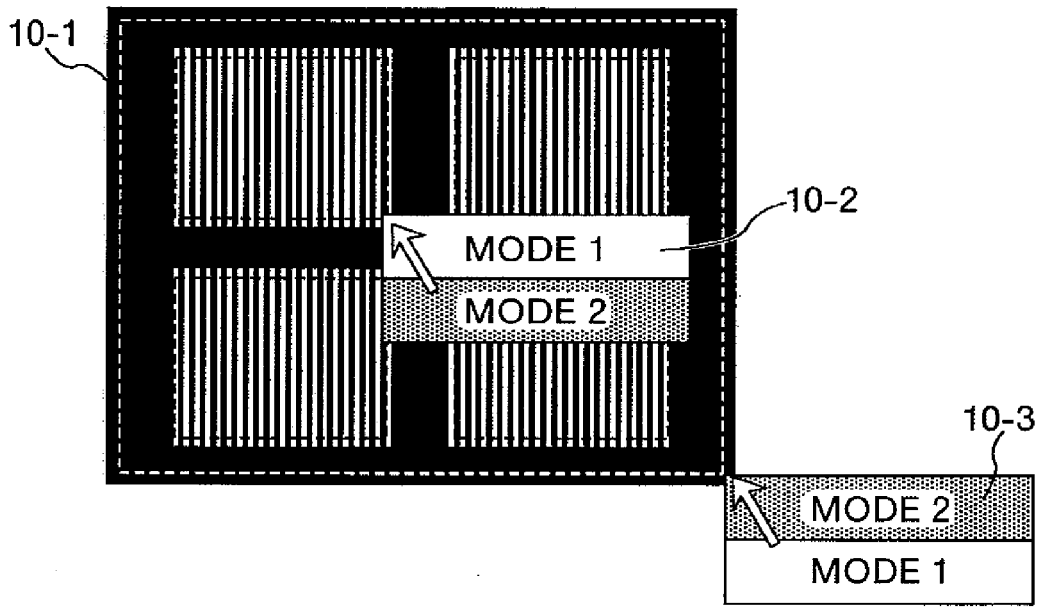
FIG. 10A is a schematic diagram of a setup method for multiple defect judgment operations.

FIG. 10A illustrates a setup method of multiple defect judgment operations. Four rectangular vertically-striped areas inside a chip 10-1 are memory mats, and the rest of the area is a peripheral circuitry area. The user specifies inspection modes for particular areas as in mode selection boxes 10-2 and 10-3 with the use of a displayed image of the chip 10-1 or its blueprint. In this example, the mode selection box 10-2 is used to set inspection mode 2 for the upper left memory mat, and the mode selection box 10-3 is used to set inspection mode 1 for the entire area of the chip 10-1. It thus follows that the two modes are set for the upper left memory mat inside the chip 10-1. Therefore, the order of priority is set in advance for areas which are subjected to a double setup. When inspection mode 2 is to be prioritized for the upper left memory mat, inspection mode 1 applies to all the area except the upper left memory mat. In this example, inspection modes are determined based on each rectangular area; alternatively, those can be set by selecting a representative image pattern, automatically searching for patterns similar to the representative image pattern, and labeling the similar patterns.

Figure 10B:
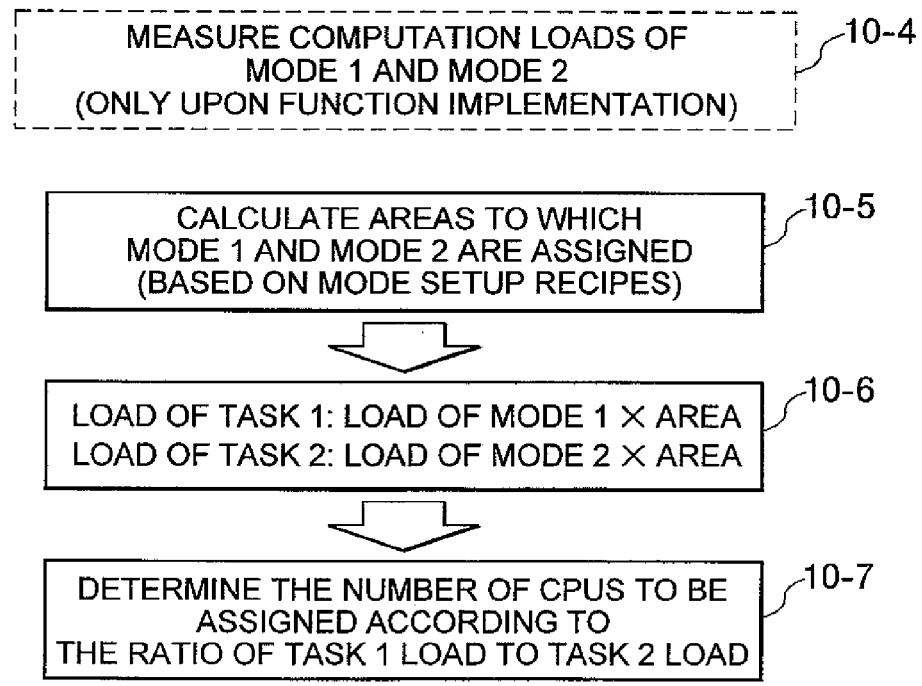
FIG. 10B is a flowchart of the setup method for multiple defect judgment operations.

In accordance with the invention, multiple defect judgment operations of different arithmetic loads can be performed efficiently. Tasks for such operations are generated by the task manager 18-1 shown in FIG. 1. FIG. 10B illustrates its process flow. When multiple defect judgment operations (hereinafter referred to as "tasks") of different arithmetic loads are set, the arithmetic loads of inspection modes are first measured in advance upon task implementation (Step 10-4). Upon the execution of the tasks, the task manger 18-1 uses the recipe set in FIG. 10A by which each of the inspection modes has been set for particular areas in the chip 10-1 to calculate the mode-assigned areas (Step 10-5). Thereafter, the arithmetic loads of the tasks are calculated with the use of the arithmetic loads of the inspection modes and the mode-assigned areas (Step 10-6). Then, the number of arithmetic CPUs to which the tasks are assigned is determined based on task load ratios, and the tasks are assigned based on the number determined (Step 10-7).

Figure 11:
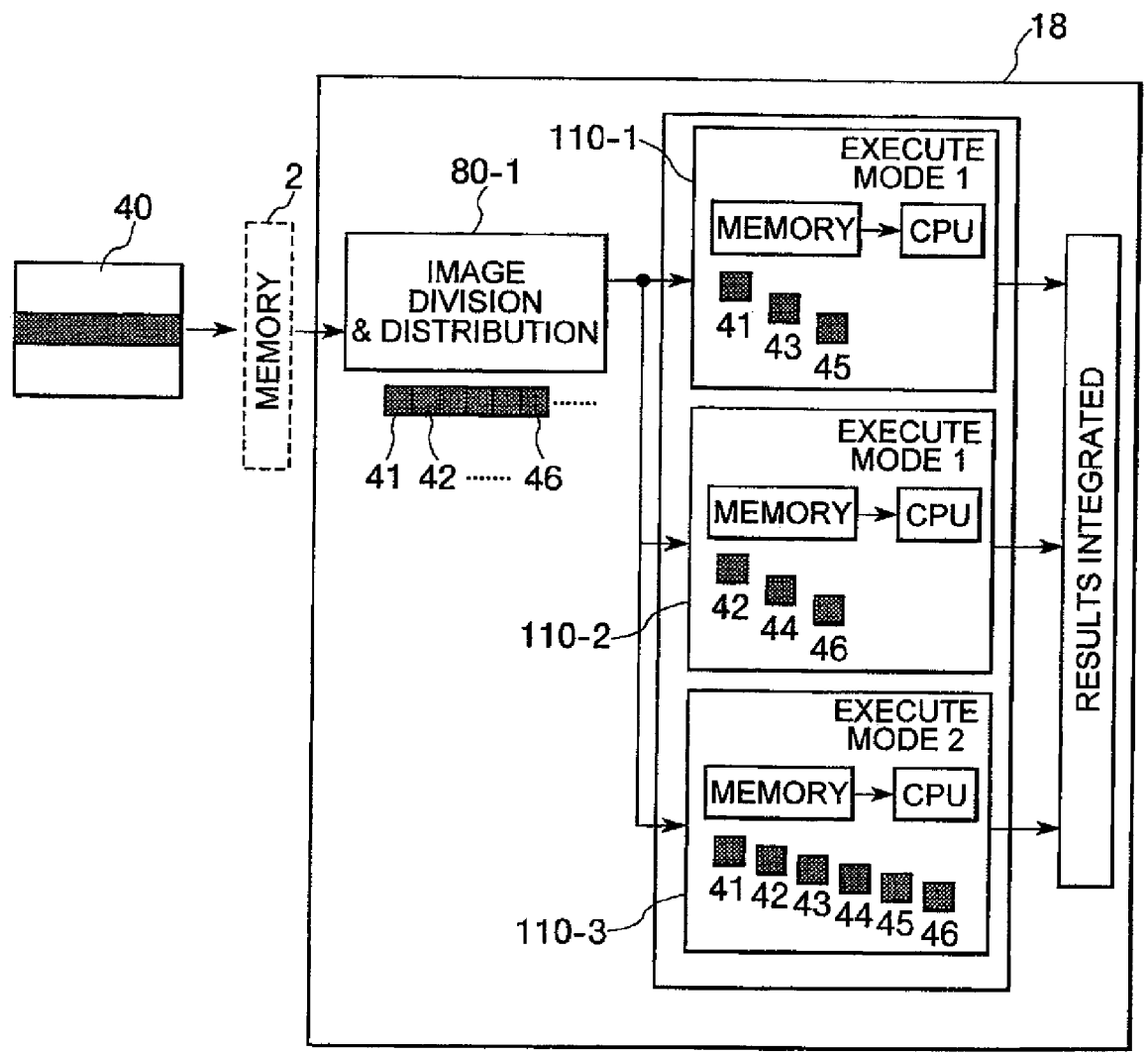
FIG. 11 is a schematic diagram illustrating the process flow of parallel operations of multiple defect judgment modes.

FIG. 11 illustrates an example in which the load ratio of task 1 to task 2 is 2:1, and defect judgment operations based on tasks 1 and 2 for all the six areas of the chip 40 are executed by three arithmetic CPUs. The task manager 80-1 divides an image of the chip 40 into six small images 41 to 46 and distributes them to CPUs 110-1 and 110-2 alternately. The task manager 80-1 also assigns execution commands of task 1 to the CPUs 110-1 and 110-2. In addition, the task manager 80-1 assigns all the divided images 41 to 46 and an execution command of task 2 to a CPU 110-3. The CPUs 110-1 to 110-3 perform defect judgment operations on the input images according to the given execution commands and then output results. Such a configuration makes it possible to complete all the tasks in substantially the same time without generating waiting time for the three CPUs 110-1 to 110-3. After the judgment results are output from the CPUs 110-1 to 110-3, they are integrated. For example, both the CPUs 110-1 and 110-3 perform defect judgment operation on the same divided image 41 and output defect candidates. These defect candidates are integrated or finalized with the use of the logical conjunction or logical disjunction of the defect candidates. By the task manager 80-1 generating such tasks, two mutually-different defect judgment operations can be performed at high speed without task setting for each area of the chip 40, thereby increasing the sensitivity of the defect inspection apparatus. Also, instead of the task manager dividing an image equally to input the equally divided images to the CPUs, it is possible to cut images of particular areas out of the image according to a defect judgment mode setup recipe as the one set in FIG. 10A and provide the CPUs with the cutout images and task commands. When a cutout image is subjected to defect judgment operation twice in that case, the result of the higher-priority inspection mode as in FIG. 10A is selected as the final result.

Although the method for efficiently executing two defect judgment operations has been described, the invention is also capable of executing three or more defect judgment operations efficiently.

Figure 12A:
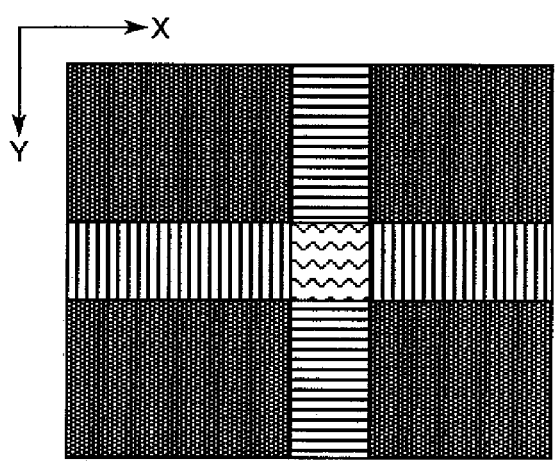
FIG. 12A is a schematic diagram of an input image when multiple defect judgment modes are employed.
Figure 12B:
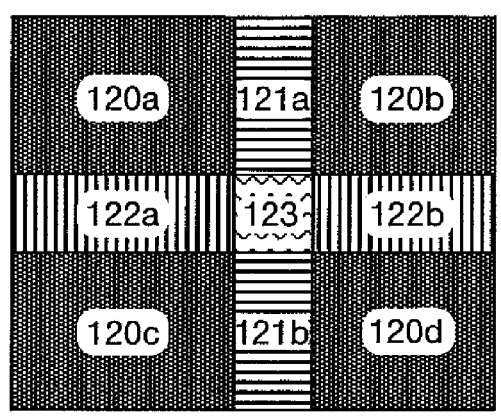
FIG. 12B a schematic diagram illustrating the pattern profiles of the input image when multiple defect judgment modes are employed.

With reference to FIGS. 12A and 12B, it is discussed when three or more defect judgment operations are effective. FIG. 12A shows an input image. According to pattern profiles, the image can be roughly classified into four areas, as shown in FIG. 12B: horizontally-striped pattern areas 121a and 121b, vertically-striped pattern areas 122a and 122b; pattern-less areas 120a, 120b, 120c, and 120d, and a random pattern area 123. In such a case, parallel execution of four defect judgment operations is effective. Because the horizontally-striped pattern areas 121a and 121b have the same patterns arranged in the Y direction of FIG. 12A, a pixel in such areas is compared in terms of luminance with a pixel located away in the Y direction from that pixel by a pattern pitch. Likewise, since the vertically-striped pattern areas 122a and 122b have the same patterns arranged in the X direction of FIG. 12A, a pixel in such areas is compared in terms of luminance with a pixel located away in the X direction from that pixel by a pattern pitch. In the pattern-less areas 120a, 120b, 120c, and 120d, pixels are simply compared with threshold values. In the random pattern area 123 at the center of the image, pixels are compared with those in a random pattern area of an adjacent chip. Parallel execution of the four defect judgment operations can be executed with ease by the task manager assigning the four operations to arithmetic CPUs and transferring cutout rectangular images and tasks for executing the operations to the arithmetic CPUs.

Figure 13:
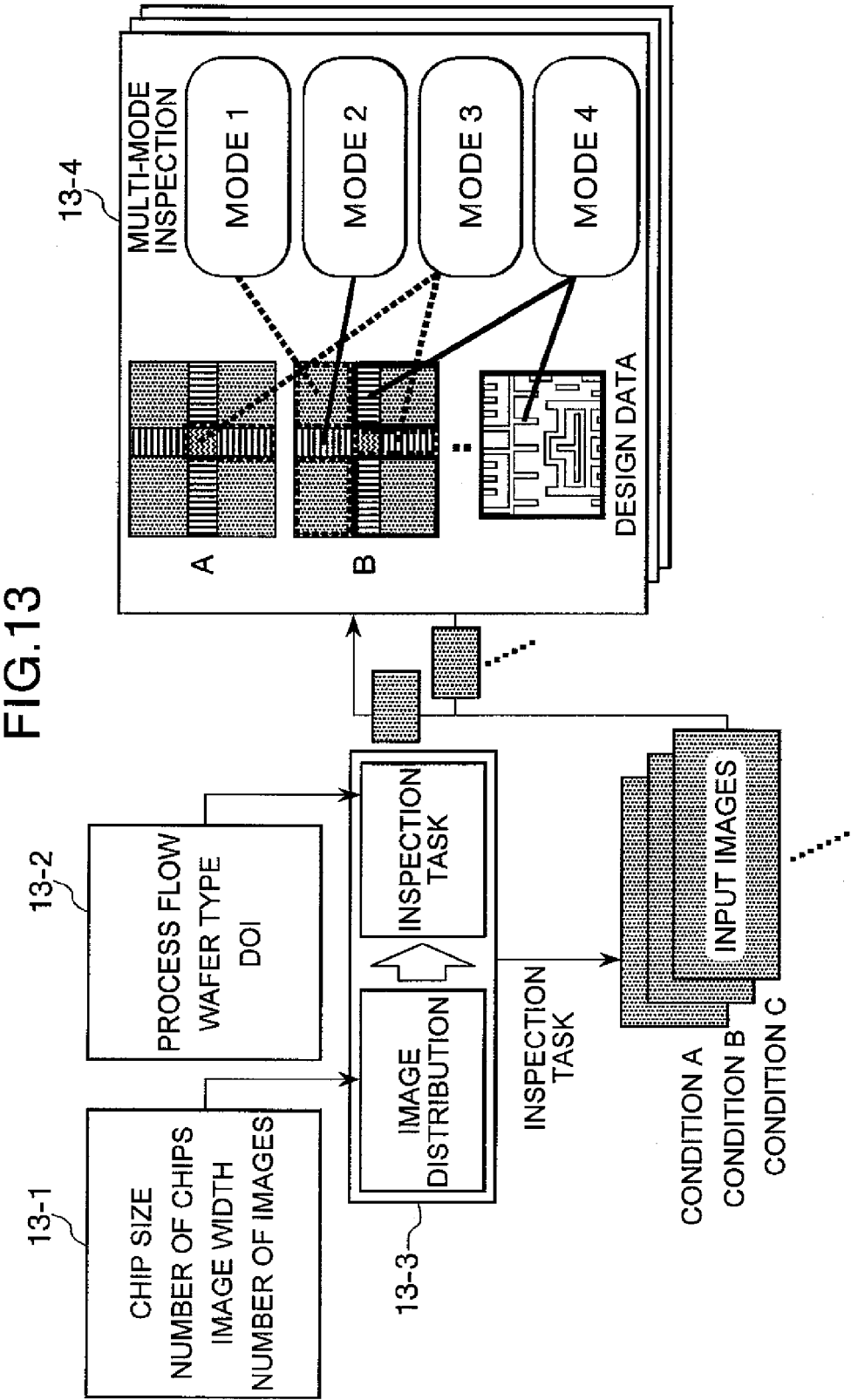
FIG. 13 schematically illustrates an exemplary configuration of a high-sensitivity defect inspection method based on inspection tasks.

FIG. 13 illustrates another exemplary configuration of the invention in which high sensitivity inspection is achieved by multiple defect judgment operations. First, a task manager 13-3 receives, as an inspection recipe, image information 13-1, such as wafer design information (memory mat layout, chip size, the number of chips) and image input information (the width of an image to be captured during one scan and the number of images of different optical conditions to be input), and wafer information 13-2, such as wafer types, process flows, and defects of interest (DOI). The task manager 13-3 then dynamically determines the proper image division number and the proper size of divided images for an efficient process. The task manager 13-3 also determines which defect judgment operation to apply to which area, based on the wafer information 13-3. Thereafter, the task manager 13-3 divides images and sets inspection tasks for the divided images to output the divided images and the set inspection tasks to arithmetic CPUs 13-4. The arithmetic CPUs 13-4 each execute the designated tasks for the divided images received. As shown in FIG. 13, one of the arithmetic CPUs 13-4 performs defect judgment operation with the use of modes 1 to 4. Mode 1 (simple binarization) is applied to pattern-less areas; mode 2 (comparison between adjacent patterns within an image) to identically-patterned areas; mode 3 (adjacent chip comparison) to random pattern areas; and mode 4 (comparison with design data) to areas prone to systematic defects. When a single arithmetic CPU performs defect judgment operation by employing multiple modes as above, it is preferred that CPU be a multi-core one, whereby each core can perform one of the modes efficiently.

Figure 14:
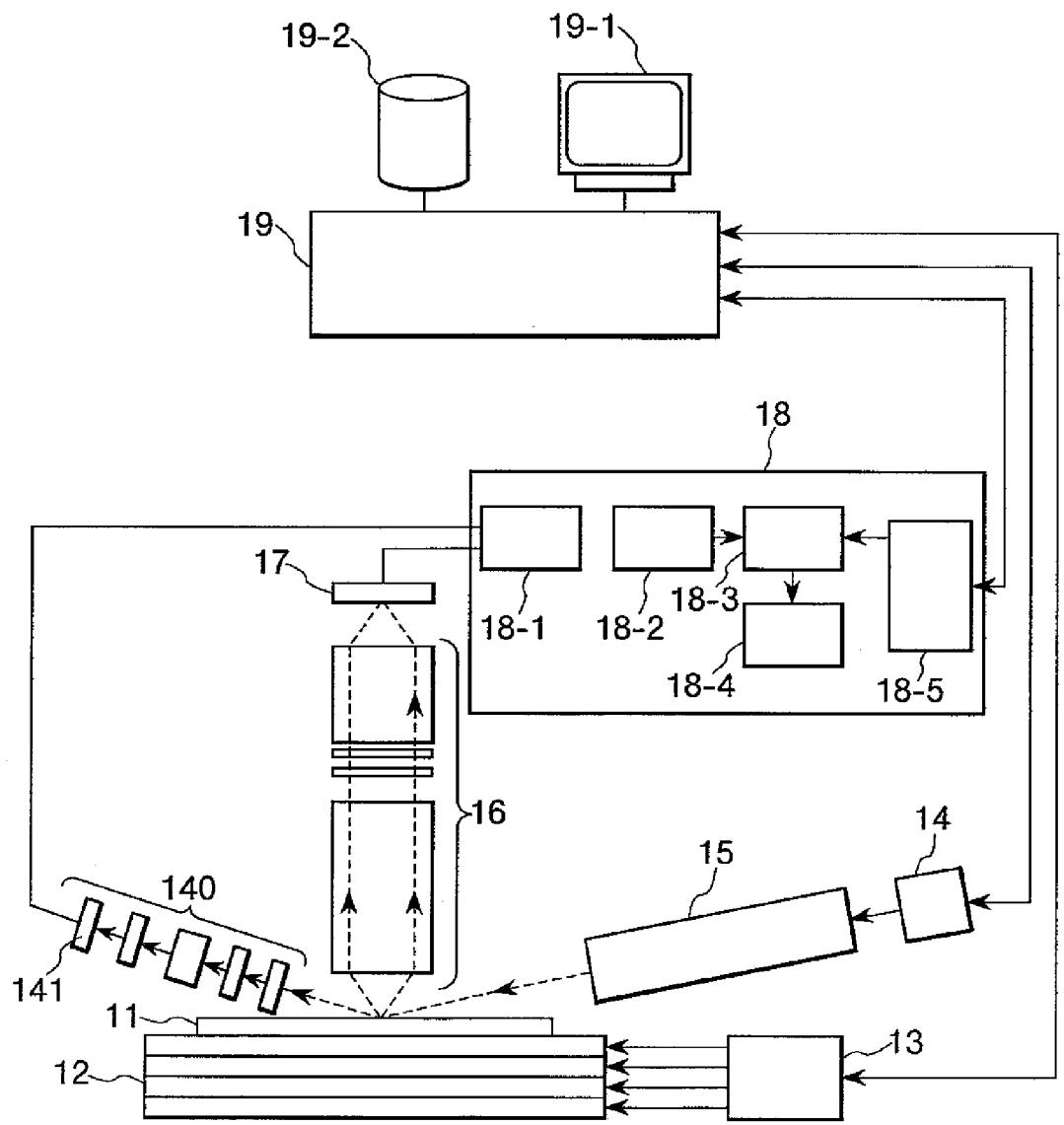
FIG. 14 schematically illustrates a defect inspection apparatus that includes multiple optical detector systems.

Although the embodiments of the invention descried so far are related to defect judgment operation in which a single detector is used to acquire images under different optical conditions, the invention is not limited thereto. Alternatively, multiple detectors can be employed to acquire images. FIG. 14 illustrates this example, showing a defect inspection apparatus constructed by adding another detector to the defect inspection apparatus of FIG. 3 that employs dark-field illumination, hence having two detectors. The identical parts shared by the two defect inspection apparatuses are assigned the same reference numerals and will not be discussed further.

The defect inspection apparatus of FIG. 14 includes an optical detector system 140 positioned obliquely with respect to the stage 12, in addition to the optical detector system 16 located above the stage 12. The optical detector system 140 focuses obliquely-scattered light from the sample 11, and an image sensor 141 receives the focused scattered light and converts it to an image signal. The obtained image signal is input to the image processor 18 for processing as image signals obtained by the detector 17 are. As can be expected, images acquired by the two optical detector systems differ in image quality, and the kinds of defects to be detected also differ partly. Thus, by integrating the information from the two optical detector systems with the use of the foregoing integration method, defects of diverse kinds can be detected. Note that a single illuminator 15 suffices for the defect inspection apparatus of FIG. 14 since the apparatus has the two optical detector systems of different optical conditions.

As stated above, as the number of optical conditions under which to acquire images increases, more pattern information can be acquired from the images; hence, more advanced distinction between defects and noise is possible. At the same time, this necessitates increasing the scale of image processing due to more data to be processed and increases costs as well. To avoid this, an alternative method is to select three or four optical conditions that are effective in distinguishing between defects and noise or in detecting defects of interest while having means to acquire images of diverse kinds by increasing the parameter ranges of the optical conditions.

Figure 15:
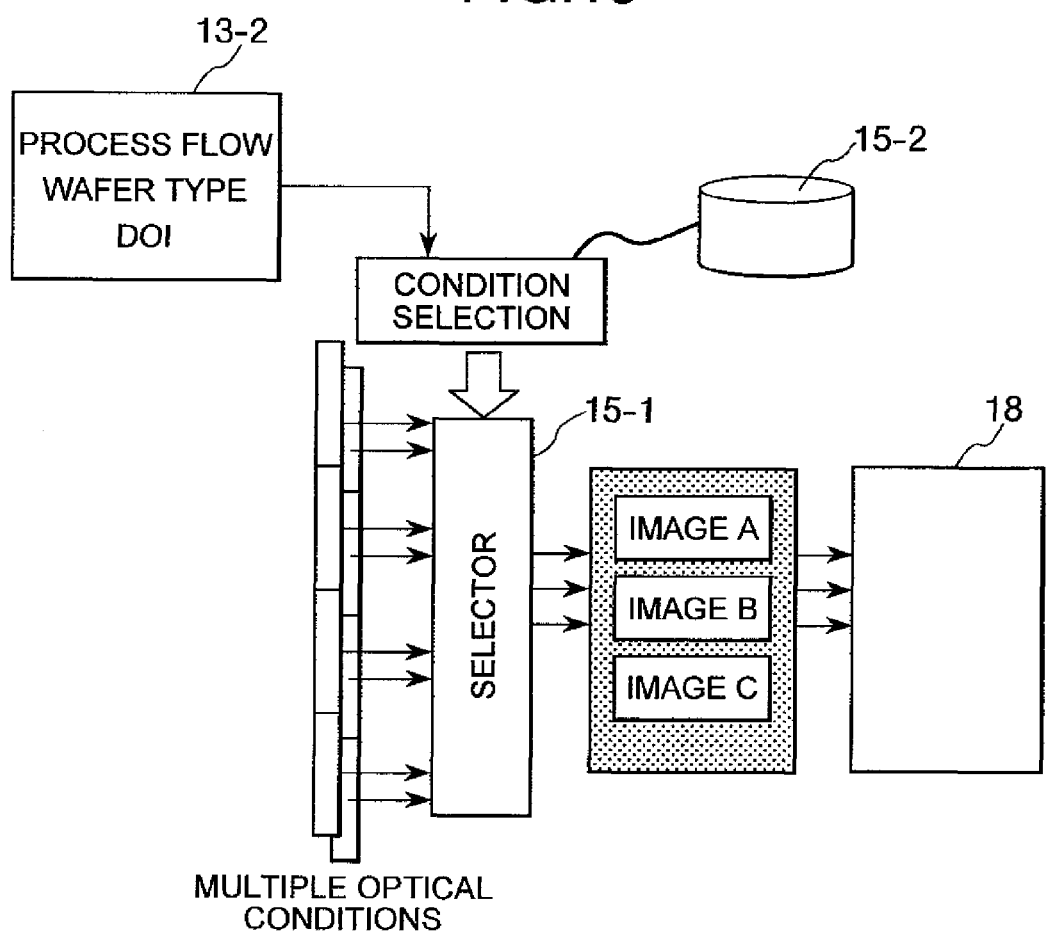
FIG. 15 is a schematic diagram illustrating an example of narrowing down multiple optical conditions.

This selection of optical conditions is now discussed with reference to FIG. 15. Sixteen or more images of different optical conditions can be acquired collectively with such a detector as shown in FIG. 5B. At the subsequent stage of the detector, a selector 15-1 is provided, as shown in FIG. 15. After receiving the wafer information 13-2 such as wafer types, process flows, and defects of interest (DOI), the selector 15-1 selects three or four optimal optical conditions with the use of the wafer information 13-2 and a database 15-2. The selector 15-1 then outputs the images of the selected optical conditions to the image processor 18. Note that the database 15-2 is created by accumulated data and simulation results. In accordance with the above method, advanced distinction between defects and noise is possible without increase in image processing scale and costs.

In the defect inspection apparatuses of the various embodiments of the invention, an image processor is constructed with multiple arithmetic CPUs and a task manager that generates tasks to perform various operations efficiently and dynamically assigns images and the tasks to the arithmetic CPUs. Thus, complex operations can be executed at high speed. In addition, various defects can be detected with high sensitivity by integrating images of multiple optical conditions to detect outlier values in feature spaces. The defect detection with high sensitivity can also be achieved by the task manager selecting the optimal defect judgment operation for each area of a chip image from among multiple defect judgment operations and causing the arithmetic CPUs to execute the selected defect judgment operations. It should be noted that although the chip comparison upon defect judgment operation according to the embodiments of the invention has been described with reference to FIG. 2A, in which a defect detection image and a reference image are the images 23 and 22, respectively, the reference image can instead be created with the use of the average of multiple adjacent chips (for example, the average of the images 21, 22, 24, and 25). It is also possible to compare the defect detection image 23 with the images of those chips (i.e., 23 with 21, 23 with 22, 23 with 24, and 23 with 25) and statistically process all the comparison results to detect defects.

In accordance with the invention, defects ranging in size from 20 nm to 90 nm can be detected regardless of a subtle difference in pattern thickness after a planarization process such as chemical-mechanical planarization (CMP) or the like and of a major luminance difference between chips to be compared due to reduction in the wavelength of illumination light.

In accordance with the invention, defects ranging in size from 20 nm to 90 nm can be detected also in inspection of low-k films such as inorganic insulating films (films of $SiO_2$, SiOF, BSG, SiOB, and porous silica) and organic insulating films (films of methyl-$SiO_2$, MSQ, polyimide, parylene, Teflon®, and amorphous carbon), regardless of local luminance differences within such films due to variation in in-film refractive-index distribution.

While the foregoing embodiments of the invention are intended for image comparison with the use of defect inspection apparatuses that employ dark-field illumination to inspect semiconductor wafers, the invention is not limited thereto. The invention can also be applied to image comparison in electron-beam pattern inspection, for example. The invention is further applicable to pattern inspection apparatuses that employ bright-field illumination. Further, inspection targets according to the invention are not limited to semiconductor wafers, but include TFT substrates, photomasks, printed circuit boards, and the like as long as defect detection is based on image comparison.

Representative effects of the invention can be summarized as below.

1) A defect inspection method and a defect inspection apparatus can be provided that are less subject to the influences of luminance variation between compared images arising from the difference in layer thickness or pattern width and capable of detecting with high sensitivity defects which would otherwise be regarded as noise.

2) By executing multiple kinds of defect judgment operations, various defects can be detected with high sensitivity that would otherwise be regarded as noise. For example, systematic defects that are likely to occur at the same area of each chip and defects located at the edge of a wafer can be detected.

3) The multiple defect judgment operations can be executed in parallel and at high speed by determining the number of arithmetic CPUs to be employed according to the load of each of the defect judgment operations.

The present invention can provide a defect inspection method and a defect inspection apparatus that are less subject to the influences of luminance variation between compared images arising from the difference in layer thickness or pattern width and are capable of detecting with high sensitivity defects which would otherwise be regarded as noise.

The invention may be embodied in other specific forms without departing from the spirit or essential characteristics thereof. The embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

The invention claimed is:

1. A defect inspection method comprising of:
illuminating laser light to a sample;
detecting scattered light from the sample;
acquiring an image based on the scattered light;

dividing the image into a plurality of areas;
setting an inspection mode corresponding to the plurality of areas;
assigning a number of CPUs based on a ratio of product computed by multiplying an arithmetic load of each area by an arithmetic area of each area; and
processing assigned CPUs and extracting defects.

2. The defect inspection method of claim 1, wherein the processing step for extracting defects based on the inspection mode set by the dividing step.

3. The defect inspection method of claim 1, wherein when dividing the image into the plurality of areas, if a plurality of inspection modes are set for a same region of the sample, at least one of the plurality of inspection modes is based on a predetermined priority.

4. The defect inspection method of claim 1, wherein when dividing the image into the plurality of areas, setting the inspection mode to a representative region of the sample and setting the same inspection mode to a similar region to the representative region of the sample.

5. A defect inspection apparatus comprising of:
an illuminating system for illuminating laser light to a sample;
a detecting system for detecting scattered light from the sample; and
a processing system comprising;
an acquiring unit for acquiring an image based on the scattered light;
a dividing unit for dividing the image into a plurality of areas;
an inspection unit for setting an inspection mode corresponding to the plurality of areas;
an assigning unit for assigning a number of CPUs based on a ratio of product computed by multiplying an arithmetic load of each area by an arithmetic area of each area; and
a calculating unit for calculating assigned CPUs and extracting defects.

6. The defect inspection apparatus of claim 5, wherein the processing system for extracting defects based on the inspection mode set by the dividing step.

7. The defect inspection apparatus of claim 5, wherein when dividing unit divides the image into the plurality of areas, if a plurality of inspection modes that are set up by the inspection unit are set for a same region of the sample, at least one of the plurality of inspection modes is based on a predetermined priority.

8. The defect inspection apparatus of claim 5, wherein when dividing unit divides the image into the plurality of areas, setting the inspection mode by the inspection unit to a representative region of the sample and setting the same inspection mode to a similar region to the representative region of the sample.

* * * * *